United States Patent [19]

Esemplare et al.

[11] 4,082,862
[45] * Apr. 4, 1978

[54] PROCESS FOR THE PRODUCTION OF RUBBER ARTICLES HAVING IMPROVED SLIP COATING

[75] Inventors: Pascal E. Esemplare, Mountainside, N.J.; Dennis Beeferman, Brooklyn, N.Y.

[73] Assignee: Sutures Inc., Coventry, Conn.

[*] Notice: The portion of the term of this patent subsequent to Jun. 29, 1993, has been disclaimed.

[21] Appl. No.: 733,399

[22] Filed: Oct. 18, 1976

Related U.S. Application Data

[60] Division of Ser. No. 589,677, Jun. 24, 1975, Pat. No. 4,027,060, which is a continuation-in-part of Ser. No. 405,863, Oct. 12, 1973, Pat. No. 3,919,442.

[51] Int. Cl.$^2$ .............................................. B32B 25/08
[52] U.S. Cl. .................................. 427/133; 264/306; 428/494; 428/500; 427/385 B; 2/168
[58] Field of Search .................... 2/168; 264/306, 307; 428/212, 334, 339, 494, 500, 517, 519, 520, 521, 522; 427/133, 385 B

[56] References Cited

U.S. PATENT DOCUMENTS

| 3,286,011 | 11/1966 | Kavalir et al. | 264/306 |
| 3,298,034 | 1/1967 | Szeguari | 2/168 |
| 3,411,982 | 11/1968 | Kavalir et al. | 264/307 X |
| 3,856,561 | 12/1974 | Esemplare et al. | 264/306 X |
| 3,919,442 | 11/1975 | Esemplare et al. | 264/306 X |
| 3,967,014 | 6/1976 | Esemplare et al. | 264/306 X |

*Primary Examiner*—Michael R. Lusignan
*Attorney, Agent, or Firm*—Larson, Taylor and Hinds

[57] ABSTRACT

In the coating of rubber surfaces with adherent slip coatings the need for release agents is avoided by selecting as the slip coating a synthetic polymer latex composition consisting essentially of about 5 to 95% by weight of a film-forming, non-elastomeric synthetic polymer component (1) having an elongation of at least about 200% and about 5 to 95% of a normally solid, non-elastomeric, synthetic polymer component (2) exhibiting an elongation of below about 20% and a coefficient of friction of up to about 0.20, said slip coating having an elongation of at least about 200 up to 700%, a coefficient of friction of up to about 0.25 and a thickness of below about 0.005 inch.

7 Claims, No Drawings

PROCESS FOR THE PRODUCTION OF RUBBER ARTICLES HAVING IMPROVED SLIP COATING

This is a divisional application of application Ser. No. 589,677, filed June 24, 1975, now U.S. Pat. No. 4,027,060, patented May 31, 1977, which in turn is a continuation-in-part of application Ser. No. 405,863, filed Oct. 12, 1973; now U.S. Pat. No. 3,919,442, patented Nov. 11, 1975.

BACKGROUND OF THE INVENTION

This invention relates to rubber articles having improved slip coatings and to methods of providing same. More particularly, the invention relates to rubber articles, such as sterile surgeons' gloves, which are provided with an improved slip coating. Still more particularly, the invention relates to such articles and methods wherein the slip coating is a non-elastomeric synthetic resin layer which when applied to the rubber substrate takes on the elastomeric characteristics of the rubber substrate.

It has previously been proposed to provide slip finishes on rubber articles such as rubber gloves or girdles by various methods. For example, the surface of a rubber glove can be halogenated with bromine or chlorine to make it slippery. However, this treatment may result in very poor aging properties. Discoloration can begin almost immediately and, within a month, the halogenated surface may become hard and brittle and brown in color. This can be avoided only by taking great care in the halogenation process and even then there is no assurance of obtaining a uniform, subtained, slip film. Waxes and silicones have been used but these provide only a temporary solution as these materials rub off in a very short time. It has further been proposed in U.S. Pat. No. 3,286,011 issued Mar. 18, 1964, and U.S. Pat. No. 3,411,982 issued Mar. 18, 1964, to provide a slip finish comprising a rubber latex and a resin latex. While such coatings reduce the coefficient of friction of the rubber article to a slight extent, it is desirable to further reduce the coefficient of friction. For example, it is desirable to further reduce the coefficient of friction to make it easier to put on and take off a rubber article such as a rubber glove.

In our copending application Ser. No. 220,692, we have disclosed an excellent resin slip finish for rubber articles. The resin used is a vinyl chloride-alkyl acrylate copolymer or a vinylidene chloride-alkyl acrylate copolymer. While the slip finish is excellent, it may produce a "cobblestoning" effect when the rubber article is stretched to a large extent, of for example, over 450 percent. In surgeons' gloves, for example, stretchability of 700 percent is desired. Where gloves in accordance with our earlier invention are stretched to that extent, they tend to cobblestone, a condition which is not desirable in use.

Also, in the preparation of rubber articles by dipping a form into a rubber latex followed by coagulation of the rubber latex into the desired article, it has heretofore been necessary to first apply to the form a coating of a release agent such as a mold release powder, e.g., talc, diatomaceous earth, etc., or a lubricant type release agent, e.g., glycerine. The reasons for the use of the release agents are (1) to prevent damage to the rubber article when it is stripped from the form and/or (2) to preclude the tendency of the tacky rubber to self adhesion when the article is removed. Use of release agents in the preparation of dipped rubber articles, however, is not without its shortcomings for it naturally leads to adulterated final products which have trapped or otherwise picked up the release agent on the coagulated rubber surface. Nevertheless, the contaminated rubber article is a matter which manufacturers of such articles have had to live with for it has not been possible to obtain these rubber articles in a commercially acceptable form without the use of the release agents.

Another shortcoming commonly associated with the use of release agents in the manufacture of rubber articles is that the process requires clean up of the residue of the release agent on the mold or form after formation of each and every article, a tedious and time-consuming operation.

The same problems necessitating the use of release agents in the formation of rubber articles directly on dipping forms, likewise necessitate the use of release agents in processes such as described in U.S. Pat. No. 3,411,982 to Kavalir et al., wherein the slip-coated rubber articles are prepared by first providing a release composition onto the form before it is dipped into the rubber latex. In addition to the aforementioned stripping and self-adhesion difficulties, there is a tendency for the slip coating to separate from the rubber substrate when release agents are not utilized in such processes.

Furthermore, in the prior art processes for obtaining slip coatings there has been a tendency for the surface of the articles produced to exhibit streaks.

Thus, it is the object of the invention to provide rubber articles containing slip coatings on at least one surface thereof which slip coatings are comprised of non-elastomeric materials which when applied to the rubber substrate take on the elastomeric properties of the rubber substrate.

It is also an object of the invention to provide non-elastomeric slip coated rubber substrates which can be stretched a very large amount without separation of the rubber and slip coat phases.

Yet another object of the invention is to provide a process for the production of rubber articles which process does not require the use of release agents as a separate and distinct entity and which nevertheless results in a rubber article having a slip coating which has an appreciably lower coefficient of friction than the rubber surface to which it has been applied.

A further object of the invention is to provide a process for obtaining slip coatings on rubber articles characterized by being free of streaking.

BRIEF SUMMARY OF THE INVENTION

The foregoing and other objects which will be apparent to those having ordinary skill in the art are achieved according to the present invention by providing an article comprising a rubber surface provided with an adherent slip coating of a synthetic polymer latex composition consisting essentially of about 5 to 95% by weight of a film-forming, non-elastomeric synthetic polymer component (1) having an elongation of at least about 200% that of the rubber surface and about 5 to 95% of a normally solid, non-elastomeric, synthetic polymer component (2) exhibiting an elongation of below about 20% and a coefficient of friction of up to about 0.2, preferably up to about 0.15 said slip coating having an elongation of at least about 200 up to about 700%, a coefficient of up to about 0.25 and a thickness of below about 0.005 inch.

These slip coatings are provided according to the present invention by utilizing instead of the conventional release agents the above described slip coating synthetic polymer latex composition. The rubber surface is merely contacted directly with the synthetic resin latex and the coating thus provided is permitted to form a slip coating on the rubber surface.

In a preferred embodiment of the invention, after the rubber is formed over the slip coating and the coagulant for the rubber removed as by water washing, the resulting composite is provided another coat of said resin mixture. After drying, the resin-rubber-resin composite thus formed is easily stripped off the form to provide a resin-protected article having a slip coating that reduces the coefficient of friction of the rubber surface to which it is applied and which can be stretched a very large extent without separation of the resin slip coating from the rubber. In the case of surgeons' gloves there is thereby produced a glove which can be easily slipped on and off and which does not have the external tackiness that characterizes conventional surgeons' gloves. The slip coating is the release agent which is now intrinsic to the glove itself and not an unwanted contaminent.

DETAILED DESCRIPTION OF THE INVENTION

The rubber surface on which the slip coating is provided may be fabricated from any suitable conventional latex dipping compound such as those disclosed in U.S. Pat. No. 3,411,982. The latex may be pre-cured or non pre-cured latex in which case the rubber article is cured after forming. The latex dip may contain conventional compounding ingredients commonly utilized. Specific examples are given in U.S. Pat. No. 3,411,982. The rubber may be natural rubber or any conventional latex suitable for dipping operations. Of the various natural and synthetic latices, natural rubber, polychloroprene rubber, synthetic polyisoprene, SBR, and mixtures thereof are preferred. Conventional formulations for each of these rubbers are well known in the art and those skilled in the art are readily able to vary the formulations and conditions of curing and the like to suit the particular latex being used as well as the particular final article desired. Similarly, the article can vary widely and includes gloves, particularly surgeons' gloves, girdles, and the like.

The synthetic resin latex composition utilized according to the present invention includes a first polymer component and a second polymer component. The first polymer component is a film-forming non-elastomeric synthetic polymer having an elongation of at least about 200 up to 700% without break. By a "non-elastomeric" polymer as used herein and in the appended claims is meant a polymer which at about room temperature can be stretched but which does not exhibit reversal behavior. When fully stretched, that is, stretched to within the elongation limit, such polymers do not recover their original dimensions fully on release of the stress. In general, the non-elastomeric synthetic polymers are normally solid polymers of relatively low molecular weight usually ranging from about 25,000 to 1,000,000.

The first polymer component of the invention may be a homopolymer, an interpolymer (by which is meant a polymer of two or more monomers), mixtures of homopolymers, mixtures of interpolymers or mixtures of homopolymers and interpolymers. Illustrative of preferred interpolymers are vinyl chloride-alkyl acrylate copolymer, vinylidene chloride-alkyl acrylate copolymer, and vinyl acetate-alkyl acrylate copolymer. By "alkyl acrylate" is meant alkyl esters of acrylic or methacrylic acid. The alkyl group is preferably methyl, ethyl, propyl, or butyl and butyl is preferred. The copolymer includes from 5 to 95 mole percent of the vinyl chloride, vinylidene chloride, or vinyl acetate units and, correspondingly, from 95 to 5 mole percent of the acrylate units. Preferably, the former units comprise from 70 to 90 mole percent of the copolymer and the acrylate units correspondingly comprise from 30 to 10 mole percent of the copolymer. Other copolymers suitable for use as the first non-elastomeric polymer component include, for instance, ethylene-vinylchloride copolymer, ethylene-vinylacetate copolymer, ethylene-ethylacrylate copolymer, ethylene-butylacrylate copolymer, ethylene-acrylic acid copolymer, acrylic-rubber polymers, olefinic copolymers such as ethylene/propylene copolymer, silicone polymers, silicone/acrylic copolymers and the like. The copolymer may also include up to 5 molar percent, preferably from ½ to 5 mole percent, based on the total amount of the other units, of acrylic acid or methacrylic acid units. The copolymer may also include any of the conventional vinyl resin plasticizers in amounts of generally up to about 5 mole percent. Suitable plasticizers include tricresyl phosphate, dibutyl phthalate, dibutyl sebacate, tributyl phosphate, dioctyl phthalate, trioctyl phosphate, dioctyl sebacate, dioctyl adipate, low molecular weight polymers such as poly(propylene glycol) esters, and the benzoate plasticizers such as 2-ethylhexyl-p-oxygenzoate.

Illustrative of homopolymers which can be used as the first non-elastomeric polymer component are polyethylacrylate, polybutylacrylate and polyoctylmethacrylate.

Physical blends of homopolymers suitable for use as the first polymer component include, for instance, blends of homopolymers of the monomers of the preferred copolymers described above. Such mixtures include blends of from about 5 to 95%, preferably about 70 to 90%, by weight, of polyvinyl chloride, polyvinylidene chloride or polyvinyl acetate and about 90 to 10%, preferably 30 to 10%, by weight, of polyalkylacrylate.

The second polymer component of the synthetic polymer latex composition is a normally solid, non-elastomeric, synthetic polymer which has an elongation of below about 20% and a coefficient of friction of up to about 0.20. It may or may not be a film-forming polymer and can be either a homopolymer, an interpolymer or mixtures thereof. Mixtures of more than one homopolymer or interpolymer can be used if desired. Preferred second polymer components are copolymers of vinyl chloride or vinylidene chloride and a vinyl ester. By "ester" is meant alkyl esters of monocarboxylic acid having from 2 to 4 carbon atoms. Suitable vinyl esters include vinyl acetate, vinyl propionate, vinyl butyrate, and the like, and the copolymer of vinyl acetate and vinyl chloride is preferred. The copolymer includes from 90 to 10 mole percent, preferably 40 to 60 mole percent, of the vinyl or vinylidene chloride units, and, correspondingly, from 10 to 90 mole percent, preferably 60 to 40 mole percent, of the vinyl ester units. As in the case of the first copolymer component, the second copolymer component may also contain up to 5 mole percent, preferably ½ to 5 mole percent, of acrylic acid or methacrylic acid to improve adhesion and may likewise include a conventional plasticizer in amounts of generally up to 5 mole percent.

Among the homopolymers suitable for use as the non-elastomeric second polymer component can be included polyvinyl acetate, polymethylmethacrylate, polystyrene, polyvinyl chloride, polyvinylidene chloride, polyesters such as polyethyleneterephthalate, polyamides, polyaldehydes, polyolefins including polyhalohydrocarbons, etc.

Preferred physical blends of homopolymers for use as the second polymer components are blends of homopolymers of the monomers of the above-described preferred copolymers, i.e., blends of about 10 to 90%, preferably about 70 to 90%, by weight, of polyvinylchloride or polyvinylidene chloride and about 10 to 90%, preferably about 40 to 60% by weight of polyvinyl ester.

The first polymer component constitutes at least 5 percent by weight (solids basis) of the two resin components. Where the first resin component is present in an amount of less than 5 percent, stretching to a large extent will start to result in cobblestoning. Where the amount of the first resin component exceeds 95 percent by weight (solids basis) of the two resin components, the slipperiness of the coating tends to suffer. Good results are obtained when the first resin component is present in an amount of from 5 to 75 percent by weight and best results are achieved when it is present in an amount of about 20–30 percent by weight, the second component making up the balance. Other materials can be included in the synthetic polymer latex composition as long as they do not unduly deleterious affect the novel characteristic provided by same. For instance, the synthetic latex composition of the invention can tolerate below about 20% by weight of rubber.

The synthetic polymer latex composition comprised of the first and second polymer components and constituting the slip coat of the invention has an elongation of at least about 200 up to 700% and a coefficient of friction up to about 0.25, preferably up to about 0.20. The thickness of the slip coat should be below about 0.005 inch, preferably below about 0.001 inch. Coefficient of friction as used herein and the appended claims is measured by attaching a section of film to the bottom of a steel "sled" (2½ × 2½ × ¼ inch) and pulling horizontally over a polytetrafluoroethylene surface. The ratio of force required to pull the sled to the weight of the sled may be taken as the coefficient of friction (coeff. friction = F/W).

The improved slip coating according to the invention is preferably provided on a rubber surface by contacting the rubber surface with an aqueous latex consisting essentially of water and the two polymer resins. Alternatively, the slip coating can be first provided on a form and the form subsequently dipped into a rubber latex as disclosed in U.S. Pat. No. 3,411,982.

The slip coating provided by the present invention has excellent characteristics of slipperiness. A simple way to demonstrate the slipperiness of rubber coated according to the invention is to place two coated rubber surfaces together and rub the coated rubber surfaces back and forth while grasped between the fingers. Previous slip coatings which have been tested slip poorly when held in this manner. However, the coatings provided by the present invention show a marked slip. Furthermore, the coatings provided by the present invention are tenaceously adhesive and the rubber substrate can be stretched to maximum extent without affecting the slipperiness of and without causing cracking of the slip coating according to the present invention.

According to a preferred embodiment of the present invention a form for the desired article is preferably heated and provided as by dipping with an aqueous latex consisting essentially of water and the two polymer components. The resin coating is dried on the form and provided with a coagulant such as a solution of calcium nitrate and isopropanol after which it is dipped into a tank containing rubber latex solution. The rubber latex solution generally varies from 25 to 40% solids depending upon the thickness and the viscosity of the desired product. The immersion into the tank will vary depending on the desired thickness and in general the dip time will extend from about 3 seconds to 1 minute. After the formation of the rubber substrate the coagulant therein is leached, for instance, by dipping the resulting form into a leach tank containing hot water which is usually at a temperature ranging from about 135° to 140° F.

At this stage of the process in its broadest aspects, the article may be stripped off the form but only if the rubber surface is provided with a protective coating of one of the aforementioned conventional release agents such as, for instance, talc or glycerine. In this instance there results a product one surface of which contains the resin slip coating on one side of the substrate and a protective coating of the conventional release agents on the opposite side. It is preferred, however, to continue the process by the application of a second coating of the resin of the invention by applying to the rubber substrate an aqueous latex consisting essentially of water and the two vinyl copolymers. The second resin slip coating is then dried and the resin-rubber-resin composite cured and stripped off the form. Preferably the form is dipped into hot water for 10 to 15 minutes to assist in the removal of the article from the form.

The following examples are included to further illustrate the process of the present invention.

EXAMPLE I

A clean glove form is first utilized to make conventional surgeons' gloves from natural rubber by dipping the form into an aqueous natural rubber latex composition made by mixing 3 parts by weight of a conventional 60% solids natural rubber latex (e.g., Lotol L 9241) in 2 parts by weight of water. Immersion of the form is fairly slow but withdrawal is rapid so that there is streaming of latex down the form. At the point where the thumb of the form starts to emerge from the latex, the form is tilted to a slight angle so that the latex runs between the thumb and first finger. At the point where the form is completely out of the latex, the form is tilted in the opposite direction. The form is then reverted to the vertical position and allowed to drain from the finger tips until no further dripping takes place. The form is then rotated so that the fingers are up. The form is then dipped into coagulant solution comprising 20% acetic acid in isopropyl alcohol, removed and allowed to dry at room temperature approximately 2 to 3 minutes. The form is again dipped into the natural rubber latex. Dwell time is 5 to 10 seconds. The dwell time in this step determines the gauge of the glove. Withdrawal of the form is done in the same manner as described above. The form is dipped into the coagulant again, removed and allowed to dry at room temperature approximately 2 to 3 minutes.

The form is now dipped into an aqueous composition made by dispersing 5 parts by weight of a 50% solids content synthetic resin latex in 4 parts by weight of water. The synthetic resin is a conventional solid synthetic resin copolymer of approximately equi-molar amounts of vinyl chloride and butyl acrylate and also containing about 3 mole percent acrylic acid units along the polymer backbone. The dwell time in the synthetic resin latex is about 30 seconds. Withdrawal of the form is done in the same manner as described above. The form is then dried for approximately 60 minutes in a forced air oven maintained between 180° and 185° F. The gloves are now stripped from the form in hot water and placed in a hot water (190° to 200° F) leaching tank now immersed into a leach tank at 135° F for one-half hour. The purpose for the leach tank is to leach out the surfactants and the calcium nitrate. After removal from the leach tank the excess water is shaken from the forms and the forms are dipped into the slip coating latex for 30 seconds, then removed from the dipping tank and rotated in a full circle to even out the coating. The coated form is then placed in a forced air oven at 195° for 45 minutes. The gloves are then stripped from the forms in cold water and then washed in a washing machine for 20 minutes having an overflow rate of 30 gal/hr. After washing, the gloves are then placed in a tumble dryer at 135° F for 1 hour. Results using various combinations of resins are as follows:

| Ex. | First Resin | Component Amount (parts by weight) | Second Resin | Component Amount (parts by weight) | Solids content % by weight | Slip | Extensibility |
|---|---|---|---|---|---|---|---|
| II | A[1] | 1 | B[2] | 9 | 5 | excellent | excellent |
| III | A | 2 | B | 8 | 5 | " | " |
| IV | A | 3 | B | 7 | 5 | " | " |
| V | A | 4 | B | 6 | 5 | " | " |
| VI | A | 5 | B | 5 | 5 | " | " |
| VII | A | 6.5 | B | 3.5 | 10 | good | " |
| VIII | A | 6.5 | B | 3.5 | 5 | " | " |
| IX | A | 6.5 | B | 3.5 | 2.5 | " | " |
| X | A | 15 | B | 5 | 20 | good[3] | " |
| XI | A | 15 | B | 5 | 17.64 | " | " |
| XII | A | 15 | B | 5 | 15 | " | " |
| XIII | A | 15 | B | 5 | 10 | " | " |
| XIV | A | 15 | B | 5 | 5 | " | " |
| XV | A | 15 | B | 5 | 2.5 | " | " |
| XVI | A | 15 | B | 5 | 1 | " | " |
| XVII | A | 17 | B | 3 | 10 | fair | " |

Notes.
[1]Copolymer of vinylidene chloride (90 mole %) and butyl acrylate (10 mole %)
[2]Copolymer of vinyl chloride (40 mole %) and vinyl acetate (60 mole %)
[3]The slip of Examples 10-16 is good, but not quite as good as that of Examples VII-IX.

for 12 to 16 hours, followed by drying at 180°-185° F for 1 hour.

The gloves are then turned inside out such that the slip coating is on the inside and are tested for slipperiness in two ways. First, the gloves are repeatedly put on and removed. Second, with the slip coating surfaces innermost, the palm area of the glove is grasped between the fingers and, with grasping pressure applied, the fingers are rubbed back and forth whereupon the inner glove surfaces, if sufficiently slippery, will slip relative to each other. This example is in accordance with our earlier application Ser. No. 220,692. The gloves are very easily put on and taken off and, in the grip test, even under heavy grasping pressure, the inner surfaces easily slip. However, when the gloves are stretched over about 450%, the film loses its extensibility and gives a cobblestoning effect.

EXAMPLES II-XVII

A clean glove form is first utilized to make conventional surgeons' gloves from a natural rubber latex by placing the glove form in a forced air oven at 190° F for 20 minutes. The form is then dipped into an isopropanol solution containing 20% calcium nitrate and 5% diatomaceous earth. The calcium nitrate is the coagulant and the diatomaceous earth is used as a release agent of the rubber from the form. The heated form is dipped and then removed from the coagulant bath and the alcohol is allowed to evaporate about 1 minute. The form is then immersed slowly and allowed to dwell for 8 seconds in the natural rubber latex and then the form is withdrawn slowly from the latex tank — the form are then rotated in a full circle to even out the deposition of latex on the form. The coagulated rubber on the form is The results of Examples II-XVII show that tenaciously adherent resin slip coatings having excellent extensibility are achieved according to the present invention without the necessity of utilizing rubber in the slip coat. Elongation of over 450 percent, even over 600 percent, or 700 percent, is obtainable without adverse affect on the slip coating. As indicated above, resins other than those in the working examples can be used as the first and second resin components to give similar results. Each of the resin copolymers is preferably made up of at least 20 mole percent of each of the specified units making up the polymer chain. The first and second components may each be one or more of the specified copolymers. In the case of vinyl acetate-alkyl acrylate copolymers, these may be cross linked with a conventional cross linking agent such as N-methylol acrylamide.

EXAMPLE XVIII

A clean glove form of bisque porcelain is initially heated in an oven for 15 minutes at 175° F. The heated form is then dipped into a resin coating tank for 3 seconds which tank contains a blend of 70% by weight of a copolymer of vinyl chloride (49 mole %) and vinyl acetate (61 mole %) and 30% by weight of a copolymer of vinylidene chloride (90 mole %) and butyl acrylate (10 mole %) at a total solids content of 5-10% by weight depending upon the withdrawal speed. The dipped forms are then withdrawn from the tank and then rotated to throw off the excess of coating material. There remains a drop of coating solution at the tip of each finger which drops are removed by blotting each fingertip with a blotting cloth. The forms are then placed back into the oven at 175° F for 10 minutes, removed and dipped into a coagulant tank consisting of a solution of 20% calcium nitrate and isopropanol, withdrawn and rotated to throw off excess material and aid in drying the forms. The forms are then dipped into a rubber latex tank consisting of a rubber latex solution of from 25 to 40% solids depending on viscosity and thickness of the final glove. The length of time determines the thickness and varies generally from about 3 seconds to 1 minute. After formation of the rubber substrate the forms are placed into a leach tank containing water at 135°–140° F for 20 minutes after which the forms are removed and the cuffs rolled up to form a bead. The forms are then placed in the oven at 250° F for 10 to 15 minutes, withdrawn and again dipped back into the resin tank. The forms are rotated after removal to throw off excess material and tips of the fingers are blotted as described above. The forms are placed in an oven at 210° F for ¾ of an hour to dry and cure the gloves. After the glove is cured the forms are removed from the oven and placed in a hot water tank at 135° F for 10 to 15 minutes to aid in the removal of the rubber gloves from the forms. The forms are removed from the tank and the gloves are stripped from the forms and tumble dried at 125° F. The resulting gloves are tested for slipperiness in two ways. First, the gloves are repeatedly put on and removed and second, the palm area of the glove is grasped between the fingers and with grasping pressure applied, the fingers are rubbed back and forth whereupon the inner glove surfaces, if sufficiently slippery will slip relative to each other. The gloves are very easily put on and taken off and in the grip test, even under heavy grasping pressure, the surfaces easily slip and have excellent "feel" in use. Moreover, their use eliminates contact between rubber and the surgeon's hand and thus eliminates what many surgeons believe is the cause of irritation.

The gloves are also tested for extensibility and elongations of over 450%, even over 600%, or 700%, are obtainable without separation of the slip coat phase from the rubber phase.

EXAMPLE XIX

The process of Example XVIII is repeated substituting a copolymer of vinyl acetate (75 mole %) and butyl acrylate (25 mole %) crosslinked by N-methylol acrylamide for the copolymer of vinylidene chloride and butyl acrylate. A glove of similar properties is obtained.

EXAMPLES XX–XXI

The process of Example XVIII is repeated substituting for the vinyl chloride/vinyl acetate copolymer and the vinylidene chloride/butyl acrylate copolymers, the following polymer components (1) and (2) respectively.

|  | Polymer Component (1) | Polymer Component (2) |
|---|---|---|
| Example XX | 50/50 polyvinyl chloride/polybutylacrylate admixture | 50/50 polyvinylidene chloride/polyvinyl acetate |
| Example XXI | 50/50 polyvinylidene chloride/polybutylacrylate admixture | 50/50 polyvinylidene chloride/polyvinyl acetate |

In each case a glove of similar properties is obtained.

It is claimed:

1. In a process for the production of rubber articles having a slip coating on at least one surface thereof, wherein a form is first coated with a release agent, a slip coating composition is provided on said release agent coated form and a rubber substrate is thereafter formed over said slip coating, the improvement which comprises eliminating the need for said coating of release agents by selecting as said slip coating composition a mixture of polymeric resins consisting essentially of about 5 to 95% by weight of a film-forming, non-elastomeric synthetic polymer component (1) having an elongation of at least about 200% and about 95 to 5% by weight of a normally solid, non-elastomeric, synthetic polymer component (2) exhibiting an elongation of below about 20% and a coefficient of friction of up to about 0.20, said slip coating having an elongation of at least about 200 up to 700%, a coefficient of friction of up to about 0.25 and a thickness of below about 0.005 inch.

2. The process of claim 1 wherein said rubber article is a sheet-like rubber article.

3. The process of claim 1 wherein said sheet-like rubber article comprises a rubber glove.

4. The process of claim 3 wherein said rubber glove is a sterile material rubber surgeons' glove.

5. The process of claim 4 wherein both the inside surface and outside surface of said glove are provided with a slip coating of a synthetic polymer latex composition consisting essentially of about 5 to 95% by weight of a film-forming, non-elastomeric synthetic polymer component (1) having an elongation of at least about 200% and about 5 to 95% of a normally solid, non-elastomeric, synthetic polymer component (2) exhibiting an elongation of below about 20% and a coefficient of friction of up to about 0.20, said slip coating having an elongation of at least about 200 up to 700%, a coefficient of friction of up to about 0.25 and a thickness of below about 0.005 inch.

6. The process of claim 1 wherein the form is a bisque ceramic form.

7. The process of claim 6 wherein the bisque ceramic form is a bisque porcelain form.

* * * * *